United States Patent [19]
Gulliford et al.

[11] 4,041,385
[45] Aug. 9, 1977

[54] ON-LINE SAMPLING SYSTEM FOR MONITORING PARTICLES SUSPENDED IN A FLUID

[75] Inventors: Henry Howard Gulliford; Harvey John Dunstan, St. Albans, both of England

[73] Assignee: Coulter Electronics, Inc., Hialeah, Fla.

[21] Appl. No.: 679,219

[22] Filed: Apr. 22, 1976

Related U.S. Application Data

[63] Continuation of Ser. No. 476,408, June 5, 1974, abandoned.

[51] Int. Cl.² .................... G01N 27/00; G01N 1/20
[52] U.S. Cl. .................... 324/71 CP; 73/422 R; 137/251
[58] Field of Search .................... 324/71 CP, 30 B; 23/253 A; 137/117; 73/42 A, 422 R, 422 TC, DIG. 8, 61 R, 61.1 R

[56] References Cited

U.S. PATENT DOCUMENTS

| 127,592 | 6/1872 | Gates | 137/251 |
|---|---|---|---|
| 2,585,060 | 2/1952 | Wallace | 324/30 B |
| 2,687,185 | 8/1954 | McChesney | 324/30 B |
| 3,259,981 | 7/1966 | Coulter et al. | 324/71 CP |
| 3,444,463 | 5/1969 | Coulter et al. | 324/71 CP |
| 3,549,994 | 12/1970 | Rothermel et al. | 324/71 CP |

*Primary Examiner*—John K. Corbin
*Assistant Examiner*—W. H. Punter
*Attorney, Agent, or Firm*—Silverman & Cass

[57] ABSTRACT

Method and apparatus for providing a concentration study of particles in a large system of continuously flowing fluid which is coupled to a sampling chamber that has a detector of the Coulter type therein. A regulator is provided to maintain constant the pressure in the sampling chamber irrespective of pressure changes in the large system. The regulator establishes a boundary surface between fluid from the sampling chamber and a column of liquid, such as mercury, immiscible with said fluid and of greater density than said fluid; whereby, a predetermined pressure is produced at said surface and permits sample fluid to pass through said column liquid as the pressure on the fluid variably exceeds the pressure at the boundary surface.

16 Claims, 1 Drawing Figure

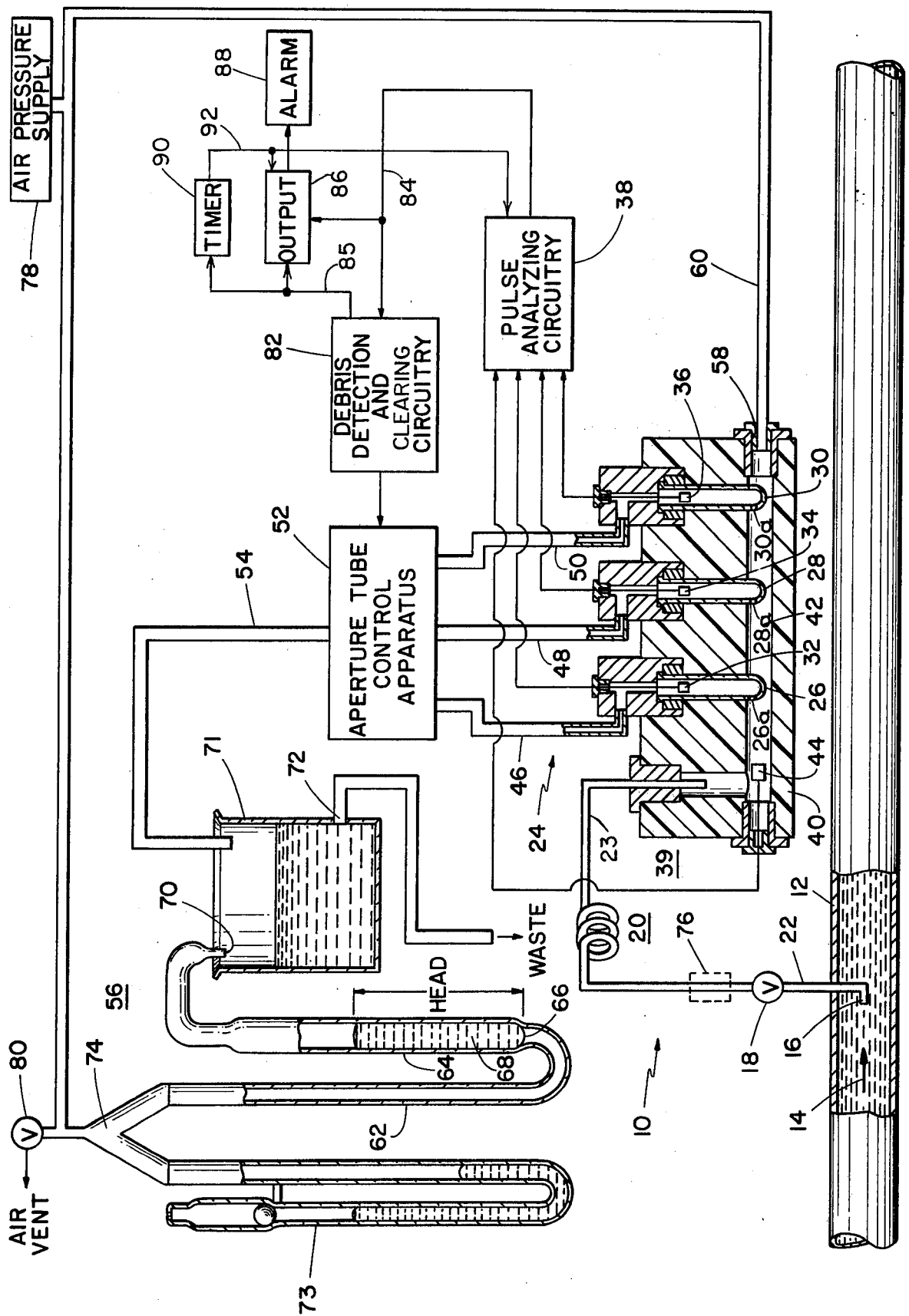

ON-LINE SAMPLING SYSTEM FOR MONITORING PARTICLES SUSPENDED IN A FLUID

This is a Continuation of application Ser. No. 476,408 Filed June 5, 1974, now abandoned.

BACKGROUND OF THE INVENTION

This invention generally relates to fluid studying systems and in particular to a novel system for continuously sampling particles in a large system of continuously flowing fluid that is subject to pressure variations.

In the study of particles suspended in a fluid medium such as may be occasioned in counting blood cells or the determination of particle concentration in other body fluids, or the size distribution of particles in a suspension, it is necessary to provide some degree of control of the flow of suspension sample through the detecting system. The degree of control will affect materially the accuracy of determination.

Particle analyzing devices of the type marketed under the registered trademark "Coulter Counter", operating under the Coulter principle disclosed in U.S. Pat. No. 2,656,508 and improved according to the teachings of U.S. Pat. No. 3,259,842, are used in such a study and respond to a particle size by producing a discrete amplitude related pulse.

There is no need to explain the Coulter principle at length, other than to state that particles in a conductive fluid are passed through a microscopic aperture in the wall of an aperture tube. A constant vacuum is applied to the aperture tube to maintain a constant volume of fluid flow through the aperture for a given period of time. Electrodes are placed on both sides of the aperture and connected to detecting means responsive to any change in the electrical character of the fluid contained within the effective volume of the aperture. The change of electrical character may be a change of resistance or impedance and it has been found that the changes very nearly are proportional to the volume and hence the size of particles passing through.

There presently is a need for providing a reliable study of particles in a large system of fluid flow. For example, such a need has been shown to exist in the oil industry which requires an on-line monitoring system for monitoring the size of particles in filtered sea water that is pumped into the ground to force the oil up.

The proper monitoring of a fluid requires a continuous sample of the fluid to be taken from a main line of fluid flow. The pressure within the line may vary and the fluid within the line may contain varying amounts of debris.

The utilization of a Coulter type particle detector requires a constant pressure differential at the aperture of the aperture tube of the detector. The pressure changes within the main line will cause changes in the differential pressure at the aperture. Such changes lead to inaccuracies in the volume of fluid passing through the aperture which causes error in measurement. Pumps could be used to provide a continuous sample of fluid to the detector except that the pressure at the output of a fluid pump is not relatively constant due to the noise and turbulence created by the pump. This noise and turbulence can cause phantom particles to be detected by the particle detector and hence an inaccurate particle count. Also, heretofore known pressure regulators were not capable of maintaining a constant pressure within the pressure variation limitations required by a Coulter type particle analyzing device. It is therefore desirable to have a regulator which maintains approximately constant the differential pressure at the aperture of an aperture tube despite changes in the pressure or velocity of the fluid from which the sample is being taken.

If there is debris in the fluid being sampled from the main fluid flow and the debris is large enough to cause serious blockage of the aperture of the detector, subsequent measurements become futile. It is therefore desirable to have an on-line system for continuously monitoring particles for long periods of time which continues to operate despite blockage of the fluid flow through the aperture.

CROSS REFERENCE TO RELATED APPLICATIONS AND PATENTS

Cited hereinafter are U.S. Pat. Nos. 3,259,891 and 3,444,463 which, to the extent that it may be necessary for a full disclosure of the invention, are hereby incorporated by reference.

SUMMARY OF THE INVENTION

An apparatus for providing a reliable study of particles in a large system of continuously flowing fluid. A sample of the fluid is coupled continuously to a sampling chamber which has a detector of the Coulter type therein. A regulator is provided to maintain the pressure in the sampling chamber constant irrespective of pressure changes in the large system. The constant pressure in the sampling chamber assures a desired constant flow of sample fluid through the detector.

The regulator is a subcombination of the above apparatus and comprises two chambers of different cross sectional areas having a common junction therebetween. The larger of the two chambers is filled with a fluid of greater density than the fluid being sampled. The smaller of the two chambers is coupled to the sampling chamber and is allowed to fill with sample fluid. Accordingly, the pressure in the sampling chamber is transferred to the junction of the two chambers. The pressure in the sampling chamber forces the greater density fluid into the larger chamber of the regulator. The pressure in the sampling chamber is greater than the pressure required to maintain the greater density fluid in the larger chamber, and the fluid within the smaller chamber will pass through the greater density fluid in the larger chamber to maintain an equilibrium between the two fluids at the junction of the two chambers. Accordingly, the pressure within the sampling chamber remains approximately constant.

The above described subcombination also includes an attenuator coupled between the sampling chamber and the large system which acts to reduce the turbulence in the sample fluid and eliminate air bubbles that might be suspended in the fluid.

The above described apparatus also includes a plurality of detectors of the Coulter type along with voting circuitry for determining if there is a blockage of one of the detectors. Timing circuitry is provided for allowing particles to be counted during spaced intervals of time for predetermined periods of time.

BRIEF DESCRIPTION OF THE DRAWINGS

The FIGURE is a diagram which is partially in block, section, and schematic form showing a system embodying the invention.

DETAILED DESCRIPTION OF THE PREFERRED EMBODIMENT

In the FIGURE, a system generally indicated by the reference character 10, provides an on-line particle sampling system wherein the differential pressure at the aperture of a Coulter type aperture tube remains approximately constant with changes of pressure in the main line from which the sample is to be taken. The system is capable of counting particles of the sample fluid continuously or at preset intervals for long periods of time without attendance.

A main pipe 12 contains the fluid to be sampled which flows in a direction indicated by the arrow 14. The fluid within pipe 12 is at a minimum pressure of 5 lbs. per square inch (hereinafter referred to as PSI). Sampling means comprising a small sampling tube 16, an isolation valve 18, and a flow restrictor 20 cooperate to sample fluid from the main flow of fluid in the main pipe 12. The sampling tube 16 is coupled into the main stream of fluid flow of pipe 12. The diameter of the sampling tube is in proportion to the diameter of the main pipe 12 to provide isokinetic sampling of the fluid by the sampling tube 16. The ratio of the cross-sectional area of the main pipe to the sampling tube should be the same as the ratio of the desired sampling rate to the flow rate of fluid in the main pipe. Accordingly, a representative sample of the fluid in the main pipe 12 can be taken.

The isolation valve 18 is coupled to the sampling tube 16 via a conduit 22 to allow fluid to flow from the sampling tube 16 to the flow restrictor 20. The flow restrictor 20 is comprised of a small bore tube wound in a helix. When fluid is passed through the flow restrictor, turbulence in the sample fluid and air bubbles suspended in the fluid are reduced. The output of flow restrictor 20 is coupled via a conduit 23 to particle study means generally indicated by the reference character 24. The particle study means comprise apparatus and associated circuitry for sampling and studying the particles suspended within the sample fluid coupled thereto from flow restrictor 20. A Coulter type electronic particle analyzing apparatus is included as an element of the particle study means 24. The particle analyzing apparatus includes a plurality of aperture tubes 26, 28 and 30 having electrodes 32, 34 and 36, respectively disposed therein. The electrodes 32, 34 and 36 are coupled to a pulse analyzing circuit 38. The pulse analyzing circuit 38 provides particle pulses representative of the particles passing through the apertures of aperture 26a, 28a, and 30a tubes 26, 28 and 30.

An aperture tube holding assembly, generally indicated by the reference character 39 comprises an aperture block 40 having a sampling chamber 42 in the bottom thereof. The three aperture tubes 26, 28 and 30 set in liquid-tight removable engagement into the rim of the block 40 with their bottom ends immersed in the sample fluid in the sampling chamber 42 and their apertures exposed to the fluid. The fluid obviously is required to be conductive; hence, if a nonconductive fluid is involved it may be treated to render it conductive. For example, the invention was especially designed for use in testing filtered sea water. Its use with fresh water would therefore call for adding a salt of suitable type in the fluid.

An electrode 44 is coupled to the pulse analyzing circuit 38. The aperture tubes 26, 28 and 30 respectively have output conduits 46, 48 and 50 coupled to an aperture tube control apparatus 52. For this discussion, it will be assumed that the aperture tube control apparatus 52 couples only aperture tube 26 to atmosphere via a conduit 54. For sample fluid within sampling chamber 42 to flow through the aperture of aperture tube 26, the pressure within chamber 42 must be greater than the pressure within the aperture tube. When sample fluid flows through the aperture, particles suspended within the sample fluid flow will be detected by the electrodes 32 and 44 and the pulse analyzing circuitry 38.

Assuming that the differential pressure at the aperture of aperture tube 26 remains constant, the volume of sample fluid passing through the aperture can be determined by knowing the fluid pressure differential at the aperture and also knowing the period of time the sample fluid is allowed to flow through the aperture. The pulse analyzing circuitry 38 is operated for a predetermined period of time and the particle concentration of the sample fluid can be calculated.

As described previously, one of the problems with the on-line system of sampling is that the pressure or the velocity of the fluid within the main pipe 12 will vary, which causes a pressure variation within the sampling chamber 42 which, in turn, creates the undesirable variation of the differential pressure at the aperture. To compensate for these pressure variations within the chamber 42, a regulator, generally indicated by the reference character 56, is coupled to the sampling chamber 42 via a suspension output port 58 and a conduit 60. The regulator 56 comprises two hollow members 62 and 64. Hollow member 62 has a chamber therein where has a cross-sectional area less than the cross-sectional area of the chamber within the hollow members 64. Hollow member 62 and 64 have a common junction 66. Hollow member 64 is filled with mercury 68. The mercury 68 has a greater density than the fluid within the main pipe 12. The smaller chamber within hollow member 62 is filled with sample fluid from the sampling chamber 42. The pressure within chamber 42 forces the mercury into the large chamber of hollow member 64. The pressure within chamber 42 is thereby transferred to the junction between the sample fluid and the mercury. The junction point 66 is located between hollow members 62 and 64.

The theory of operation of regulator 56 is that $x$ amount of pressure is required to push fluid through a mercury column $y$ inches high. If there is more than $x$ amount of pressure available then the excess pressure will pass through the mercury to atmosphere. The pressure $x$ is absolutely constant and its pressure is related to the head of mercury in hollow member 64. Accordingly, if the pressure within the chamber 42 is greater than the pressure required to maintain the mercury within the larger chamber of hollow member 64, the less dense sample fluid will pass through the mercury.

Hollow member 64 is provided with an exit port 70 for allowing excess sample fluid that has passed through the mercury to pass out the port 70 to waste. An equilibrium is established at the junction between the mercury column 68 and the sample fluid within hollow member 62 at the junction 66. The pressure within the chamber 42 will remain approximately constant irrespective of the changes in fluid pressure coupled to the chamber from the main pipe 14 by the sampling means. As the pressure within the chamber 42 exceeds that pressure required to maintain the head of mercury within the chamber of hollow member 64, the excess pressure will be relieved by the passage of sample fluid through the mercury and out exit port 70 to waste.

The exit port 70 of hollow member 64 is constructed to allow any particle suspension which passes through the mercury column within hollow member 64 to pass into a waste vessel 71. The waste vessel 71 has an output port 72 situated a distance above the base of the vessel 71. The placement of the output port 72 above the base of the vessel acts as a mercury trap within the vessel 71 to trap any mercury forced out of the hollow member 64 due to excessive pressure within the sampling chamber 42. The waste vessel 71 electrically decouples the particle suspension within the waste vessel from the detector of the particle study means 24.

A manometer 73 is coupled to the conduit 60 via a Y connector 74. THe manometer 73 is filled with mercury and the head of mercury formed within the manometer 73 will be representative of the head of mercury within the regulator 56. As the pressure within chamber 42 varies so will the head of mercury in the manometer 73. The manometer 73 allows for the visual inspection of the operation of the system 10.

The above described system operates to maintain the differential pressure at the aperture of the aperture tube 26 constant by maintaining the pressure within the sampling chamber 42 constant. A requirement for proper operation of this system is that the pressure within the main pipe 12 be maintained at a minimum pressure of approximately 5 PSI. If the pressure within the main pipe 12 falls below this minimum pressure, a pump 76 would be coupled between the isolation valve 18 and the flow restrictor 20, to supply the necessary minimum pressure. During actual operation of the system 10, when the pressure within the main pipe 12 was varied from 5 to 50 PSI, the head of mercury in manometer 73 varied by only 1 millimeter which represents approximately a 1 millimeter change in the differential pressure at the aperture of one of the aperture tubes. Such regulation was heretofore unavailable with known pressure regulators. Accordingly, the pressure within sampling chamber 42 was maintained approximately constant with wide pressure variations within the main pipe 12.

It also has been found that with substantial velocity changes of the fluid within the main pipe 12, there were no changes detected in the particle concentrations of the fluid sampled in the sampling chamber 42; the system 10 can compensate for velocity variations and still provide an accurate particle count.

The above described system also has the versatility of allowing sample fluids to be sampled from a container open to atmosphere. Under such a sampling condition, sample fluid is drawn into the system by the pump 76. Once a sufficient quantity of sample fluid has been drawn, the pump 76 is turned off and an air pressure supply 78 is coupled into the system via the conduit 60 to supply the necessary constant pressure to the sampling chamber 42 for creating the differential pressure at the aperture of the aperture tube 26.

An air vent 80 is coupled to the conduit 60 to allow an outlet for any air which may be trapped within the conduits of the system 10. Such a venting is referred to as "bleeding" and during the initial setting-up of the system, bleeding is performed to eliminate any trapped air within the system 10.

Debris detecting and clearing circuitry 82 is constructed in accordance with the teachings of U.S. Pat. No. 3,259,891 entitled "Debris Alarm". The debris detecting and clearing circuitry 82 controls the aperture tube control apparatus 52 by sensing when the aperture of the aperture tube is blocked. When a blockage condition occurs, the debris detecting and clearing circuitry 82 couples a signal to the aperture tube control apparatus 52 which activates a debris clearing procedure for clearing the aperture of the aperture tube that is blocked. For example, conduit 46 would be pinched shut creating a sudden back pressure at the aperture of tube 26. If the blockage continues, the debris detecting and clearing circuitry 82 will couple a control signal to the aperture tube control apparatus 52 to disengage the tube that is blocked by closing or pinching shut the conduit coupling that tube to atmosphere, preventing fluid from flowing through its aperture. Thereupon, the conduit of an unblocked tube would be opened to atmosphere, thereby allowing fluid to flow through the aperture of that tube.

The aperture tubes 26, 28 and 30 provide redundancy which allows the system 10 to operate continuously over an extended period of time despite the blockage by debris of any one or more, but less than all of the aperture tubes.

The pulse analyzing circuitry 38 produces a signal which is fed on a branched line 84 to the clearing circuitry 82 and to a pulse count output means 86. When a blockage condition occurs in an aperture, the debris detecting and clearing circuitry 82 applies an inhibit signal to a line 85 and inhibits count pulses on the line 84 from being registered in the output means 86, and thereby prevents any error in the particle concentration measurement which would result from this blockage condition. Once the blockage is cleared by the aperture tube control apparatus 52, or a different aperture tube is selected to allow fluid to pass therethrough, the inhibit condition is removed and particle count pulses again are allowed to flow to the pulse count output means 86.

The pulse count output means 86 is constructed such that a presetable pulse count value can be stored therein. In the event that such preset value is exceeded, the output means 86 feeds a control signal to an alarm device 88, which signals an alarm condition, such as by an audible signal, thereby indicating an excessive particle concentration in the fluid being analyzed.

A timer 90 is coupled to the pulse analyzing circuitry 38 and the pulse count output means 86 by a control line 92 to allow the counting of particles for preselected periods of time.

The inhibit output 85 from the voting circuitry 82 also is coupled to the timer 90, such that the timer is momentarily stopped during a blockage condition, whereby during the time that the pulse count output means 86 is inhibited from registering the particle count pulses, the timer also is inhibited. Accordingly, the concentration measurement accomplished by way of the pulse count output means 86 accurately corresponds to the measuring time duration established by the timer 90. The timer 90 allows an operator to choose a predetermined time for which particles are to be counted. For example, 4, 8 or 16 seconds can be chosen as that period of time that particles are allowed to pass through an aperture. The timer also controls the time between the particle counts to be, for example 3, 6, 12 or 24 minutes. During the time between counts, sample fluid is continuously flowing through the sampling chamber 42. Accordingly, the timer 90 allows the system 10 to run for long periods of time without attendance by an operator.

Since sample fluid is continuously flowing through the sampling chamber 42, even when the system is not actually counting particles, the fluid being sampled is continuously representative of fluid flowing in the main pipe 12.

What is desired to be secured by Letters of Patent of the United States is:

1. For use in the monitoring of a particle suspension, a method of regulating fluid pressure in a particle analyzing apparatus of the Coulter type and employing a sampling chamber for receiving a particle suspension from a large system of flowing fluid, subject to pressure variations said method serving to maintain approximately constant the pressure of suspension within the sampling chamber and comprising the steps of: placing in conjunction two chambers of different cross-sectional area, coupling the chamber of smaller cross-sectional area to the sampling chamber, whereby to introduce the particle suspension into the smaller cross-sectional area chamber, introducing into the larger cross-sectional area chamber a liquid having a density greater than that of the particle suspension so as to maintain a pressure head of the greater density liquid within the larger cross-sectional area chamber with respect to the pressure within the sampling chamber, wherein, when the said pressure head is balanced by the suspension pressure, the liquid is retained in the larger cross-sectional area chamber, and causing the particle suspension to pass through the greater density liquid when the pressure within the sampling chamber is greater than the pressure head.

2. For use in the monitoring of a particle suspension, a method of maintaining approximately constant the fluid pressure in a sampling chamber of an apparatus for monitoring a fluid particle suspension flowing continuously in a system which is subject to fluid pressure variations, which comprises: admitting into the sampling chamber sample fluid having variable input pressures from said system; establishing first and second output paths from the sampling chamber for different portions of the sample fluid admitted therein, the first output path being for a first of said portions and being for purposes of particle monitoring of that first portion, and the second output path being for a second sample portion and being for purposes of pressure control of the fluid in said sampling chamber and especially for control of the movement of said first sample portion to said first output path at least one aperture tube of the Coulter type with the aperture portion thereof being housed within said sampling chamber for recept of said first portion of the particle suspension; establishing, external the sampling chamber, a boundary surface between said second sample portion fluid exiting from the sampling chamber via said second output path and a column of liquid immiscible with said sample fluid, said liquid being of greater density than said sample fluid; generating a predetermined pressure at the boundary surface for inhibiting flow of said second sample portion from said sampling chamber via said second output path unless pressure in said sampling chamber is caused to exceed the generated predetermined pressure; and causing said sampling chamber to have an input pressure which, even though subject to said variable input pressures from said system, always exceeds the generated predetermined pressure; the input pressure attained by said step of causing thereby forcing the second sample portion to flow variably from said sampling chamber through said boundary surface and said liquid and thereupon maintaining approximately constant the fluid pressure in said sampling chamber.

3. A method according to claim 1 which includes maintaining the boundary surface at the junction of first and second chambers of different cross-sectional area, the greater density liquid being disposed in the chamber of greater cross-sectional area.

4. A method according to claim 3 including the step of placing at atmosphere pressure and physically above the level of liquid therein, the chamber with the greater cross-sectional area.

5. An apparatus for monitoring particles in suspension comprising: a sampling chamber having an input into which suspension subject to input pressure variations can be admitted continuously, said sampling chamber having a first output from which passes a first portion of particles in suspension for particle monitoring purposes, and a second output from which passes a second portion of the suspension for purposes of regulation of pressure within said sampling chamber for control of the passage of the first particle portion from said first output at least one aperture tube of the Coulter type with the aperture portion thereof being housed within said sampling chamber for recept of said first portion of the particle suspension; first and second pressure chambers having a common junction, said first pressure chamber being in communication with said second output from said sampling chamber, said second pressure chamber being adapted to receive a liquid so as to produce a pressure head at said junction, such that pressure due to the suspension in said sampling chamber is capable of sustaining said liquid in said second pressure chamber and maintaining said pressure head and, the suspension pressure by exceeding the pressure head causing suspension to flow from the sampling chamber through said second output and said liquid for maintaining approximately constant the pressure in said sampling chamber.

6. Apparatus according to claim 5, which includes debris detecting circuitry responsive to the presence of debris within said aperture portion, and debris clearing apparatus responsive to the said debris detecting circuitry for clearing debris from said aperture portion and directing the debris from said sampling chamber toward said junction.

7. Apparatus according to claim 5 including pressure means coupled to the suspension for causing its input pressure, notwithstanding the input variations thereof as received by said sampling chamber, to exceed said pressure head.

8. Apparatus according to claim 5 in which adjacent said common junction said chambers have different cross-sectional areas and said liquid has a greater density than the particle suspension.

9. Apparatus according to claim 8 including: sampling means for sampling the fluid suspension from a larger system thereof, said sampling means including flow restriction means coupled to a suspension input port of the sampling chamber for reducing the turbulence of the fluid coupled to the sampling chamber, said flow restriction means comprising a length of small bore tubing wound in a helix through which the fluid suspension is passed.

10. Apparatus according to claim 8 which includes particle concentration measuring means coupled to be responsive to the particles passing through said aperture tube.

11. Apparatus according to claim 10 in which said concentration measuring means includes timing means and particle count accumulating means for measuring the particle concentration over a predetermined period of time at predetermined intervals of time.

12. Apparatus according to claim 5 including a plurality of detectors each including a particle sensing aperture means of the Coulter type in said sampling chamber, particle monitoring means for receiving the output from the detectors, and switching circuitry interposed between said detectors and said monitoring means and responsive to outputs from said detectors for switching the detector output to said monitoring means from one detector to another detector only when one detector becomes inoperative, such as because of blockage of its aperture means.

13. Apparatus according to claim 12 including debris detecting circuitry responsive to the presence of debris within said aperture means, and debris clearing apparatus responsive to the said debris detecting circuitry for clearing debris from said aperture means and directing the debris from said sampling chamber toward said junction, said switching circuitry being activated in the event that said debris clearing apparatus is unsuccessful in maintaining operative any specific detector.

14. Apparatus according to claim 12 including timing means coupled to said detectors for allowing particles to be counted for a predetermined period of time at predetermined intervals of time and in which said timing means is coupled to be inhibited during the time that a detector is inoperative.

15. Apparatus according to claim 14 including particle concentration measuring means coupled to the output of said detectors and in which said particle concentration measuring means is controlled to be inhibited when said timing means is inhibited.

16. Apparatus according to claim 15 in which adjacent to said common junction said chambers have different cross-sectional areas, with said second chamber having the larger cross-sectional area.

* * * * *